United States Patent
Kloke et al.

(10) Patent No.: US 12,162,212 B2
(45) Date of Patent: Dec. 10, 2024

(54) METHOD FOR THE PREPARATION OF A CELL CULTURE INSERT WITH AT LEAST ONE MEMBRANE

(71) Applicant: Cellbricks GmbH, Berlin (DE)

(72) Inventors: Lutz Kloke, Berlin (DE); Alexander Thomas, Berlin (DE); Tobias Grix, Berlin (DE); Benjamin Noichl, Berlin (DE); Anna Kreuder, Linsengericht (DE)

(73) Assignee: Cellbricks GmbH, Berlin (DE)

( * ) Notice: Subject to any disclaimer, the term of this patent is extended or adjusted under 35 U.S.C. 154(b) by 907 days.

(21) Appl. No.: 17/054,810

(22) PCT Filed: May 13, 2019

(86) PCT No.: PCT/EP2019/062204
§ 371 (c)(1),
(2) Date: Nov. 12, 2020

(87) PCT Pub. No.: WO2019/219605
PCT Pub. Date: Nov. 21, 2019

(65) Prior Publication Data
US 2021/0107212 A1    Apr. 15, 2021

(30) Foreign Application Priority Data
May 16, 2018 (DE) .................. 10 2018 111 751.5

(51) Int. Cl.
*B29C 64/00* (2017.01)
*B29C 64/124* (2017.01)
(Continued)

(52) U.S. Cl.
CPC ............ *B29C 64/124* (2017.08); *B33Y 10/00* (2014.12); *B33Y 80/00* (2014.12); *C12M 25/04* (2013.01); *B29K 2995/0056* (2013.01)

(58) Field of Classification Search
None
See application file for complete search history.

(56) References Cited

U.S. PATENT DOCUMENTS

| | | | |
|---|---|---|---|
| 10,299,940 B2 | 5/2019 | Kloke | |
| 2016/0136895 A1* | 5/2016 | Beyer | B33Y 30/00 425/132 |
| 2019/0143002 A1 | 5/2019 | Denda et al. | |

FOREIGN PATENT DOCUMENTS

| | | |
|---|---|---|
| EP | 2548943 A1 | 1/2013 |
| EP | 3476933 A1 | 5/2019 |

(Continued)

OTHER PUBLICATIONS

Duregger et al., "Additive-manufactured microporous polymer membranes for biomedical in vitro applications", Journal of Biomaterials Applications, 2018, 18 pages.

(Continued)

*Primary Examiner* — Jyoti Nagpaul
(74) *Attorney, Agent, or Firm* — The Webb Law Firm

(57) ABSTRACT

A method for producing a cell culture insert with at least one membrane, in particular at least one biological membrane, may include the following steps: providing at least one insert blank with at least one opening; and forming the at least one membrane in the insert blank by means of a bio-printing method.

19 Claims, 13 Drawing Sheets

(51) Int. Cl.
     *B33Y 10/00*     (2015.01)
     *B33Y 80/00*     (2015.01)
     *C12M 1/12*     (2006.01)

(56) References Cited

FOREIGN PATENT DOCUMENTS

| WO | 2016057571 A1 | 4/2016 |
| WO | 2016075103 A1 | 5/2016 |
| WO | 2016179242 A1 | 11/2016 |
| WO | 2017222065 A1 | 12/2017 |
| WO | 2018064323 A1 | 4/2018 |

OTHER PUBLICATIONS

Femmer et al., "Print your own membrane: direct rapid prototyping of polydimethylsiloxane", Lab on a Chip, 2014, 12 pages.
Horvath et al., "Engineering an in vitro air-blood barrier by 3D bioprinting", Scientific Reports, 2015, 17 pages.
Low et al., "Perspective on 3D printing of separation membranes and comparison to related unconventional fabrication techniques", Journal of Membrane Science, 2017, pp. 596-613.

\* cited by examiner a)

b)

1

2

3

4

5

6 blank for hanging blank with feet three dimensional architecture with one material | Three dimensional architecture with two materials blank for hanging blank with feet blank for hanging blank with feet functional material introduced point wise    functional material introduced flat blank for hanging blank with feet

METHOD FOR THE PREPARATION OF A CELL CULTURE INSERT WITH AT LEAST ONE MEMBRANE

CROSS-REFERENCE TO RELATED APPLICATIONS

This application is the United States national phase of International Application No. PCT/EP2019/062204 filed May 13, 2019, and claims priority to German Patent Application No. 10 2018 111 751.5 filed May 16, 2018, the disclosures of which are hereby incorporated by reference in their entirety.

BACKGROUND OF THE INVENTION

Field of the Invention

The disclosure relates to a method for the production of a cell culture insert with at least one membrane, in particular a biological membrane, and a cell culture insert produced according to this method.

Description of Related Art

Investigations and tests of cell cultures on a large scale are performed in multiwell plates as standard. For the cultivation of single-layer cell grasses (so-called monolayers) in such multiwell plates, suitable inserts have been developed, which are generally referred to as cell culture inserts.

Cell culture inserts are practical, permeable or semi-permeable support devices with easy applicability for the investigation of both anchorage-dependent (adherent) and anchorage-independent (non-adherent) cell lines. They are designed to create a cell culture environment that is more physiological than alternative two-dimensional culture systems.

According to the standardized sizes for multiwell plates, the diameters of the cell culture inserts are also adjusted accordingly, so that they are positioned hanging in the multiwell.

The decisive part of the cell culture insert is a membrane at the bottom/base of the cell culture insert. This membrane can have different porosities and consists of an inert plastic. Cells are seeded on this membrane in everyday laboratory work. The seeded cells normally grow into a confluent monolayer. Subsequently, barrier or penetration assays can be performed.

If the plastic membrane is removed and a biopolymer is introduced in a conventional cell culture insert, a meniscus forms due to the interfacial tension. When the polymer is cured, a cell culture insert with a concave membrane is formed. This membrane cannot or only poorly be colonized with cells, since these are pulled into the center of the cell culture insert by the combination of gravity/meniscus. This way, a cell agglomeration in the middle of the cell culture insert and no confluent monolayer is created.

SUMMARY OF THE INVENTION

The proposed solution was thus based on the object of providing a cell culture insert that has a largely flat and even biological membrane without a cone.

This object is solved with a method with features as described herein and a cell culture insert produced with this method with features as described herein.

Accordingly, a method for the preparation of a cell culture insert having at least one membrane, in particular at least one biological membrane, is provided, comprising the following steps:
providing at least one hollow insert blank with at least one opening; and
forming the membrane in the insert blank using a bio-printing method.

According to an inventive variant, the method comprises the following steps:
providing at least one hollow insert blank with at least one opening,
introducing the starting materials to produce the membrane in the insert blank,
forming the membrane in a bio-printing method (e.g. by irradiation), and
removing the insert blank, leaving the formed membrane in the insert blank.

The introduction of the starting materials for membrane production into the insert blank can be done in different ways. For example, the insert blank can be placed in a container containing the starting materials for membrane production. In this case, the feedstock blank is immersed in the liquid containing the starting materials.

However, it is also possible to introduce (e.g. drip in) the liquid containing the starting materials into the insert blank. In this case, it is necessary to prevent the liquid from flowing out of the interior of the insert blank by suitable covering or sealing of the openings of the insert blank.

Accordingly, the method comprises the following steps in accordance with a further variant in accordance with the solution:
providing at least one hollow insert blank with at least one opening,
placing the insert blank in a container containing the starting materials for producing the membrane,
forming the membrane in a bio-printing method (e.g. by irradiation), and
removing the insert blank from the container, leaving the formed membrane in the insert blank.

In accordance with another variant in accordance with the solution, the present procedure comprises the following steps:
providing at least one hollow insert blank,
covering one opening of the insert blank and introducing the starting materials for producing the membrane into the insert blank through the other opening of the insert blank,
forming the membrane in a bio-printing method (e.g. by irradiation), and
removing the cover from one opening, leaving the formed membrane in the insert blank.

The insert blank used in this method is available in this variant as a separate, already prefabricated blank. The insert blank is preferably circular with a lower and an upper opening.

In a preferred embodiment, the method includes the following steps:
providing at least one circular, hollow insert blank with a lower and an upper opening;
inserting and arranging at least one circular spacer in the insert blank at a predetermined distance $h_m$ from the lower opening of the insert blank, wherein the distance $h_m$ of the circular spacer from the lower opening of the insert blank is determined by the thickness of the membrane to be produced in the (interior of the) insert blank(s);

introducing the starting materials for producing the membrane into the insert blank; e.g. by dipping the insert blank provided with at least one spacer into a container which contains the starting materials for producing the membrane, or by introducing (dropping) the starting materials directly into the insert blank provided with at least one spacer;

forming the membrane (e.g. by irradiation), and removing the spacer from the insert blank, leaving the formed membrane in the insert blank.

Thus, a method is provided with which a cone-free, flat biological membrane can be produced in a culture insert using a printer technology. This membrane is printed into an "empty" cell culture insert. For this purpose, cell culture insert blanks are provided, which can then be assembled into a biological membrane carrier by imprinting the membrane. After completion the culture insert is finished with a biopolymer membrane instead of a plastic membrane.

The advantage of a biopolymer is a better growth and an individual adaptation of the membrane to the cells to be seeded, since not every cell type can be cultivated on a plastic membrane and requires a very precise adjustment of its extracellular environment. The polymers used include all biopolymers of the so-called extracellular matrix, including collagen, hyaluronic acid, gelatine, etc.

The culture inserts that can be produced with the present method show a number of improvements over conventional cell culture inserts:

A biological membrane consisting of one or more biopolymers is provided. This provides the cells with a more physiological culture environment. The results obtained from biological experiments are much more meaningful than those that can be generated with conventional Petri dishes or cell culture inserts.

The membrane can be modified, since the physicochemical properties can be influenced by the composition of the matrix.

For example, the membrane can be generated optically transparent, which allows a non-invasive control of the cell population in real time.

Detection substances can be coupled to the matrix to detect different phenomena during the experiment.

Furthermore, different architectures can be created on the matrix.

Besides a completely flat surface, different compartments, channels etc. can be created. Furthermore, e.g. conductive elements can be pressed into the membrane to give electrical stimuli or record electrical signals from cells.

Cells, bacteria, viruses and plant germs can already be introduced into the biomembrane.

It is possible to work with more than one material type in a layer, e.g. to create areas with a modified matrix composition.

The membrane can consist of several printing layers, so that a different membrane composition can be generated not only in the X-Y plane but also in the Z plane.

The height of the membrane can be determined by the method.

In one embodiment of the present method, the insert blank used is hollow cylindrical or truncated cone shaped.

In the case of a hollow, truncated cone insert, the truncated cone has a decreasing diameter towards the lower opening (conical taper), a base surface G (upper opening) with radius R, a top surface D (lower opening) with radius r and a height hk.

The material of the insert blank is a cell- and biocompatible polymer, but especially PP, PE, PLA, PS, PC, PTFE, PVC, PMMA, PAA, PAN, PEG, PET, PU, silicones, etc.

The typical dimensions of the insert blank are based on the height and width of normal multiwell sheets. Table 1 shows the typical dimensions for conventionally used multiwall sheets.

TABLE 1

| Culture vessel | height (mm) | diameter (mm) | Area (cm$^2$) | Volume (ml) |
|---|---|---|---|---|
| 100 mm | 20 | 100 | 55 | 20 |
| 6-well | 20 | 35 | 9.5 | 16.8 |
| 12-well | 20 | 22 | 4 | 6.9 |
| 24-well | 20 | 16 | 2 | 3.4 |
| 48-well | 20 | 10 | 1 | 0.95 |
| 96-well | 20 | 6 | 0.3 | 0.35 |

The dimensions of the present cell culture insert are accordingly as follows (see Table 2):

TABLE 2

| Culture vessel | height (mm) | diameter (mm) |
|---|---|---|
| 100 mm | between 19 and 5, e.g. 15 | between 54 and 23, e.g. 44 |
| 6-well | between 19 and 5, e.g. 15 | between 34 and 23, e.g. 25 |
| 12-well | between 19 and 5, e.g. 15 | 15 between 21 and 11, e.g. 15 |
| 24-well | between 19 and 5, e.g. 15 | between 15 and 6, e.g. 10 |
| 48-well | between 19 and 5, e.g. 15 | between 9 and 2, e.g. 5 |
| 96-well | between 19 and 5, e.g. 15 | between 9 and 2, e.g. 5 |

The dimensions of the present culture inserts are not subject to any exact classification, as the dimensions of individual multiwell plates vary from manufacturer to manufacturer. Therefore, an average value for the culture inserts is given here.

Standard blanks or individually manufactured insert blanks can be used. The individual production enables the insert to be adapted to its function. Its size and shape can be varied. This can include, for example, the hanging on the cell culture insert or the shape of the foot. For example, the cell culture insert can be provided with an outward projection on its upper side or at its upper end so that the cell culture insert can be cultivated while hanging. In addition, the bottom side or bottom end of the cell culture insert (i.e. the part of the cell culture insert that touches the bottom of the multiwell plate) may have outwardly directed and angled projections (feet). This allows the cell culture insert to stand upright in the multiwell plate automatically.

In addition, recesses or grooves can be created in the plane of the biomatrix to achieve better adhesion to the cell culture insert. Furthermore, conductive elements can also be introduced into the cell culture insert in order to obtain signal derivation or sensory characteristics.

Furthermore, the rim of the insert blank can be continuous, so that media exchange is only possible via the membrane itself.

It is also possible to cut the rim. The cutout formed in this way can have a height that can be adjusted as desired, e.g. the cutout can be below the fill level of the cell medium present in the multiwell plate. Accordingly, the cutout can be used to supply the interior of the culture insert and to allow flow through the membrane support. In the latter case, there is no barrier function between the outer multiwell plate and the interior of the blank. Such a carrier serves the pure culture and not a barrier function.

In a further embodiment of the present method, the spacer to be placed in the insert blank is provided with at least one opening, which allows gas bubbles to be discharged from the subsequently produced membrane and thus prevents air bubbles from accumulating in the membrane. The opening should be provided at the edge of the spacer if possible.

This opening can also be described as a "bubble trap". The Bubble Trap is a cut-out in the spacer or an empty space in the auxiliary membrane described below, which ensures that air can flow out. The air bubble created when the insert blank is inserted into the membrane polymer solution between the spacer (or auxiliary membrane) can escape in this way. If the air were to remain under the spacer or auxiliary membrane, it would be incorporated into the matrix as an air pocket, or the matrix would not have a flat surface at this point. In order to ensure a flat settlement area, an inclusion of air must be prevented. Ideally, the Bubble Trap should be slightly filled with membrane polymer solution to ensure that all air below the spacer or auxiliary membrane is displaced.

In a further embodiment of the present method, at least one spacer is designed in the form of a stamp. Such a stamp is suitable for truncated cone or hollow cylindrical insert blanks. The height or length of the stamp determines the desired distance $h_m$ to the lower opening of the insert blank and thus the thickness of the later membrane. It is advantageous if the stamp is coated on the outer surface to prevent the membrane, especially the biomembrane, from sticking when the stamp is removed.

The material of the stamp consists of a non-adhesive polymer. Non-adhesion in this case means adhesion between the placeholder/stamp and the biomembrane during and after the printing method. The material of the stamp can be PTFE, PEG or silicone.

The use of stamps enables the batch production of cell culture inserts with membranes.

In an embodiment variant, the method comprises the following steps:
providing a single stamp or an array of multiple stamps, where the stamp or stamps are vertically oriented;
assigning at least one insert blank to each stamp, whereby the stamp is positioned centrally in the respective insert blank;
arranging a fastening mechanism to connect the insert blank with the respective stamp;
introducing the starting materials for membrane production, preferably a liquid containing the starting materials, via the free opening into the insert blank;
covering the free openings of the insert blanks, preferably with a non-stick foil (e.g. PDMS, FEP, PTFE),
forming a polymer membrane by irradiation (irradiation preferably from above through the film);
removing the cover and the fastening mechanism, and removing the stamp or the stamp array.

When assigning insert blank and stamp, the insert blank can be put over the stamp or the stamp is inserted into the insert blank. The fastening mechanism for connecting the insert blank to the respective stamp can be a clamping mechanism (e.g. made of springs), which causes a leak-proof seal from one of the openings of the insert blank, so that the (liquid) starting materials to be subsequently introduced for membrane production remain in the insert blank and do not leak.

It is also possible to change the sequence of the method steps in the batch procedure. Thus the procedure can be carried out in the following order:
providing a base, especially a foil (e.g. PDMS foil);
providing an aliquot of membrane forming starting materials at the location on the support that is intended for one insert blank at a time (use a pipette or multipipette);
arranging an insert blank around the respective aliquot of starting materials for membrane production on the support;
arranging a fastening mechanism to fix the insert blank to the base;
inserting a single stamp or an array of multiple stamps into the respective insert blank, with the stamp or stamps oriented vertically;
forming a polymer membrane by irradiation (preferably from below through the film);
removing the stamp or stamp array from the insert blank; and
removing the insert blank with the polymer membrane formed therein, leaving the formed membrane in the insert blanks.

In another embodiment, at least one spacer is designed as a disc.

The material of the disc is according to the material of the stamp. The disc is made of PTFE, PEG or silicone. The diameter of the disc corresponds to the usual cell culture insert dimensions. The thickness of the disc corresponds to the desired membrane thickness between 10 µm and 1000 µm, preferably between 50 µm and 1000 µm, especially preferably between 200 and 800 µm, even more preferably between 300 and 500 µm.

Such a disc is particularly suitable for truncated cone insert blanks with diameters decreasing towards the lower opening. Preferably, the disc lies against the inner wall of the insert blank. The diameter of the disc is individually adjustable, so that the distance of the disc from the lower opening of the insert blank is determined by the diameter of the disc; i.e. the closer the disc diameter is to the radius r of the lower opening, the smaller the distance $h_m$ between the disc and the open cover surface, whereby the distance $h_m$ defines the thickness (or height) of the membrane to be produced.

In another variant of the present method, the spacer, in particular a disc-shaped spacer, is used in combination with an auxiliary membrane.

Here the auxiliary membrane is preferably formed on the upper side of the spacer (i.e. the side of the spacer facing the upper opening), in particular the disc-shaped spacer, by introducing a liquid composition containing starting materials suitable for forming the auxiliary membrane and subsequent curing (e.g. by irradiation with light or a similar physicochemical method).

The auxiliary membrane consists of a material that can be dissolved by a physico-chemical or enzymatic method, in particular PEG, poloxamer, hyaluronic acid, chitosan, chitin, collagen, etc.

The auxiliary membrane is produced in the insert blank with the help of a printer. The insert blank is inserted into a printer, e.g. the bioprinter of the company Cellbricks, and the auxiliary membrane is produced by stereolithography. This means that the blank is placed in a liquid polymer and cured by irradiation from above and below the bed.

In addition, the auxiliary membrane can be produced by using a disc as a spacer. The insert blank is dipped into a carrier with liquid auxiliary matrix, in the bottom of which the spacer, e.g. disc, is located. The diameter of the disc fills the interior of the blank flush. When in this state the liquid matrix within the insert blank is cured by irradiation from above or below the bed, a solid auxiliary membrane is created in the insert blank. If the insert blank with auxiliary membrane is pulled out of the carrier with the liquid, uncured auxiliary matrix, the spacer remains in the vessel with the liquid auxiliary matrix. In the insert blank with the auxiliary membrane, this creates a free space between the auxiliary matrix and the end of the insert blank, which can be lined with another membrane in the next step. The auxiliary membrane can be cured in such a way that a structure is created on the underside of the auxiliary membrane, which acts as a negative for shaping the membrane to be produced subsequently.

After the auxiliary membrane has cured, the spacer, especially the disc-shaped spacer, is removed so that a stable auxiliary membrane/auxiliary layer remains in the insert blank. This auxiliary membrane contains an opening for the discharge of gas bubbles (see also "Bubble Trap" as described above).

The insert blank, which is provided with at least one auxiliary membrane, can then be placed in a container containing the starting materials for producing the membrane. The membrane is formed e.g. by irradiation (see also below), and after formation of the membrane the auxiliary membrane is removed from the insert blank by suitable physicochemical methods (e.g. dissolution), leaving the formed (flat) membrane in the insert blank.

The auxiliary membrane is completely flat, since this layer was previously produced using the spacer. In addition, the auxiliary membrane contains an incision that acts as a bubble trap. Potential air bubbles that form when the biopolymer is introduced can escape through this drain and are not retained and incorporated into the biopolymer as it cures. After the biopolymer is filled in, it is cured. Subsequently, the auxiliary membrane can be dissolved by means of a physicochemical reaction, e.g. temperature increase/decrease, pH change, dissolution, etc., so that all that remains after dissolution is a flat biopolymer membrane (apart from a small ridge caused by the bubble trap).

As already mentioned several times, the membrane, and here preferably the biological membrane, is formed after immersing the culture insert with spacer in a container containing the starting materials to produce the membrane. The starting materials are especially photopolymerizable substances.

The formation of the membrane is carried out using a bio-printing method, as described in WO 2016/075103 A1.

After placing the culture insert with spacer in the container or reaction vessel containing the photopolymerizable liquid, light radiation is focused on a first focal plane which lies within a region of the reaction vessel filled with the liquid. This light radiation is then used to create a polymerized structure in the reaction vessel. The polymerized structure is located in a first layer.

Any number of additional layers can be applied to this first layer. For this purpose, a further photopolymerizable liquid is introduced into the reaction vessel, whereby the previously produced polymerized structure is at least partially covered with the further photopolymerizable liquid. Preferably, the previously produced polymerized structure is completely covered with the further photopolymerizable liquid. Now a further light irradiation is carried out in a further focal plane which lies within an area of the reaction vessel filled with the further liquid. This further focal plane thus differs from the first focal plane at least with respect to the already produced polymerized structure or with respect to the layer of this polymerized structure.

The aforementioned steps of introducing a further photopolymerizable liquid, focusing light on a further focal plane, and producing a further polymerized structure in a further layer can now be repeated at will with further photopolymerizable liquids until the desired membrane is produced.

The layer thickness of the membrane to be produced can be adjusted as desired and adapted to the corresponding requirements. For example, the layer thickness of the membrane can be between 10 µm and 1000 µm, preferably between 50 and 1000 µm, especially preferably between 200 and 800 µm, even more preferably between 300 and 500 µm, e.g. between 310 and 325 µm.

The photopolymerizable liquid can also contain biological cells or other substances. If polymerization occurs as a result of light irradiation, the cells contained in the liquid are embedded in a corresponding polymer.

This printing method can be used to produce membranes from any polymer, preferably biopolymers.

Accordingly, the membrane can be made of the following materials or comprise: technical biopolymers, such as gelatine; alpha- and beta-polysaccharides, such as pectins, chitin, callose and cellulose; lipids, in particular membrane-forming lipids, such as phospholipids, sphingolipids, glycolipids and ether lipids; polyhydroxyalkanoates; biobased polymers, such as polylactide, polyhydroxybutyrate petroleum-based polymers, such as polyesters, in particular polyethylene glycol, polyvinyl alcohol, polybutylene adipate terephthalate (PBAT), polybutylene succinate (PBS), polycaprolactones (PCL), polyglycolide (PGA); synthetic peptides, such as recombinantly produced amino acids, amides; components of the extracellular matrix, such as collagens, fibrillin, elastin, glycosaminoglycans, in particular hyaluronic acids, heparan sulfate, dermatan sulfate, chondroitin sulfate and keratan sulfate. Preferred membrane materials are collagens, hyaluronic acid, chitosan, gelatine, PLA, PEG and combinations thereof.

In one example, the membrane consists of gelatine and collagen as additives. A suitable photoinitiator such as lithium phenyl-2,4,6-trimethylbenzoylphosphinate (LAP) is used to produce the starting materials.

In another embodiment, a safety device is provided for holding the membrane in place during use. It is preferred if the at least one securing means is in the form of a carrier consisting of different structures adapted to the membrane material, in particular of grid-shaped or spoke-shaped structures.

In a further method variant, the cell culture insert is formed from the insert blank and membrane in one piece using the printing method described above (one-pot synthesis). In analogy to the method described in WO 2016/075103 A1, the one-pot synthesis is performed additively with photopolymerizable materials. First, the base of the scaffold is printed from a first (cell-repellent) biomaterial. Subsequently, a biocompatible layer is produced from a second biomaterial. In the last step, the scaffold is completed by the edges. Both materials are processed in a single printing method.

The insert blank formed in this method comprises a (top) opening and can include a bottom. The insert blank is preferably made of a first cell-repellent biomaterial or biopolymer, such as polyethylene glycol (PEG) or one of the other possible polymer materials mentioned above for the insert blank. On the bottom of the insert blank another biocompatible and biofunctional biopolymer is incorporated as a membrane, e.g. made of gelatine, on which cell materials can grow. The combination of the two different materials creates a scaffold that can be specifically seeded with cells on the biocompatible material.

In the course of a longer cultivation period, the biomembrane may change, e.g. shrinkage or alteration by cells. In this case, the safety device, e.g. a grid, prevents the biomembrane from slipping or falling out of the culture insert. In its simplest form, the securing agent can be placed on the underside of the cell culture insert, i.e. the side that supports the membrane. The support of the securing device, e.g. a grid, is based on a simple press fit. In order to remove the locking device (and the membrane) from the culture insert afterwards, the press fit can be removed again, e.g. with a kind of cap lifter. In this case, the press fit is simply levered off.

As already mentioned above, it is possible to produce a biological membrane in a blank from two or more polymeric materials, preferably biopolymers. The materials can be arranged in different architectures. Thus, the different polymer materials can be arranged on top of each other in layers, whereby the number of layers can be freely selected. In one variant, one layer of a first polymer and one layer of a second polymer is provided. It is also conceivable that the polymer materials are arranged next to each other in one layer. Thus, a membrane section of a first polymer material can be provided in a variant, whereby the membrane section is integrated into the second polymer material (centrally), i.e. the membrane section of the first polymer material is surrounded by the second polymer material.

In a further embodiment, a three-dimensional architecture of the membrane is planned. For this purpose the membrane can be printed using a geometric form. In this way, e.g. villi, channels, hills, valleys, etc.,—also made of different materials—can be inserted. Thus, the membrane surface to be colonized can be formed with regular or irregular structures (hills, valleys).

In one embodiment at least one channel can be inserted into the membrane. The channel can be used e.g. to supply the inner compartment of the blank. The channel acts as a medium carrier with nutrient medium, which is rinsed through the channel. Cells, which are settled on the membrane in the interior of the compartment, can be supplied from the channels through the membrane.

It is still possible to introduce functional material into the membrane. For example, an additional detector, dye, enzyme, chemokine, nanoparticles or similar can be integrated into the membrane during the printing method. Over time, this material can be used for online monitoring of the cell culture. For example, cell death can be detected by a fluorescent dye or the current oxygen saturation or pH value. The functional material may or may not have contact to the inner and outer boundary layer. The functionalization can be observed by a color change, irradiation or other detectable measurement. The functional material can be inserted pointwise into the membrane material, or it can be provided in the membrane in a flat or layered form.

It is also possible and imaginable to divide the membrane surface e.g. into segments, print cell arrays or introduce gradients. Hereby it is possible to structure the membrane exactly in its thickness and surface.

Furthermore, the optical transparency can be influenced by the formulation of the biomatrix. For example, a transparent matrix can be created that allows optical control of the cell population. Thus, the transparency allows a non-invasive control of the cell population, which is not possible with a conventional cell culture application.

In addition, a (non-polymeric) further material can be introduced into the membrane and/or the blank in a defined manner. In this way, further functions can be realized, e.g. by introducing sensors, detection, conductive materials, chemicals, nanoparticles, etc.

In one embodiment, the blank is provided with at least one probe. The at least one probe, preferably two probes, can be provided on the inside and outside of the blank. By using probes, the electrical resistance can be determined, allowing conclusions to be drawn about the density of the membrane and the cell turf.

With the present method, a cell culture insert can now be produced which consists of an insert blank with at least one membrane arranged therein, in particular at least one biomembrane, wherein the at least one membrane is flat and does not have a cone; i.e. a cell culture insert with a confluent monolayer can be provided with this method.

The present cell culture insert can be used for the cultivation of different cell lines and subsequent performance of barrier or penetration assays.

Suitable target lines are all cells and cell lines that represent a barrier function, e.g. endothelial cells, trophoblasts, astrocytes, enterocytes etc. or cells and cell lines that represent a metabolic function, e.g. hepatocytes, cardiomyocytes, myocytes etc. In general, all cell types that are adherent are suitable.

BRIEF DESCRIPTION OF THE DRAWINGS

The proposed solution is explained below with reference to the FIGS. by means of several examples. It shows.

DESCRIPTION OF THE INVENTION

Figure 1:
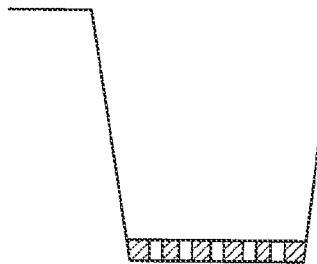
FIG. 1 shows a comparison of a conventional culture insert with pores with a culture cell insert manufactured according to the solution.
Figure 1:
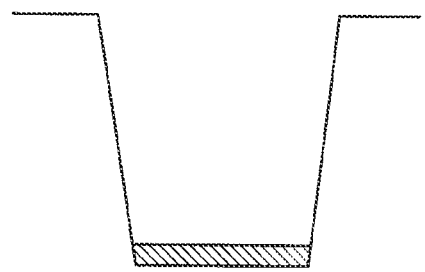

FIG. 1 shows on the left side a) a conventional cell culture insert with pores. The membrane formed at the bottom of the cell culture insert consists of an inert plastic with adjustable porosity. Cells are seeded on this membrane in the daily laboratory routine. These cells normally grow into a monolayer and can be used for barrier or penetration assays.

On the right side b) of FIG. 1, a culture insert with a biological membrane produced according to the method according to the solution is shown. The formed biological membrane is flat and has no cone. The cone-free membrane allows a good colonization with cells.

Figure 2A:
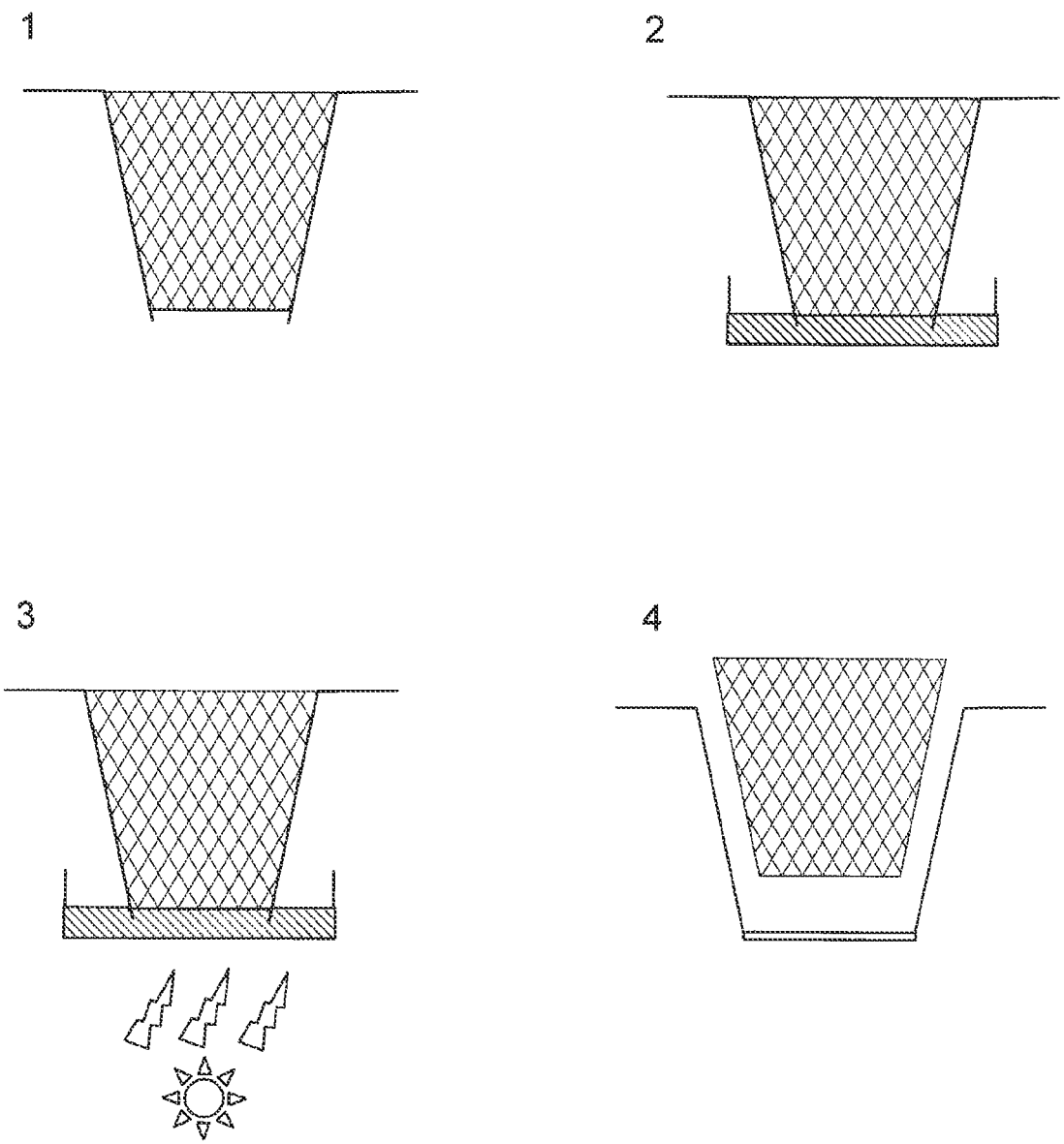
FIG. 2a shows a first embodiment of the method according to the solution.

FIG. 2a schematically illustrates a first embodiment of the procedure according to the solution, whereby a spacer, here in the form of a stamp, is inserted into a frustoconical culture insert. The height of the stamp can be adjusted individually, so that after inserting the stamp into the culture insert, the distance between the stamp and the lower opening of the culture insert can be adjusted as desired. The distance between the stamp and the lower opening of the culture insert determines the desired height or thickness of the biomembrane to be formed later. Furthermore, the stamp must be coated with a suitable material to prevent the formed biomembrane from sticking when removing the stamp from the culture insert.

In a second subsequent step, the culture insert with the stamp inserted therein is placed in a reaction vessel containing a polymerizable liquid, the polymerizable liquid containing the starting components for the production of the desired biomembrane. The stamp should contain an opening ("bubble trap") to prevent the accumulation of air bubbles in the biomembrane.

In the next, third step of the method, the biomembrane is formed in a printing method, whereby light is irradiated onto the polymerizable liquid in a focal plane, resulting in polymerization to the biomembrane in the focal plane.

After curing of the biomembrane, the stamp can be easily removed from the culture insert due to its material coating (step 4), leaving a flat biomembrane in the culture insert.

Figure 2B:
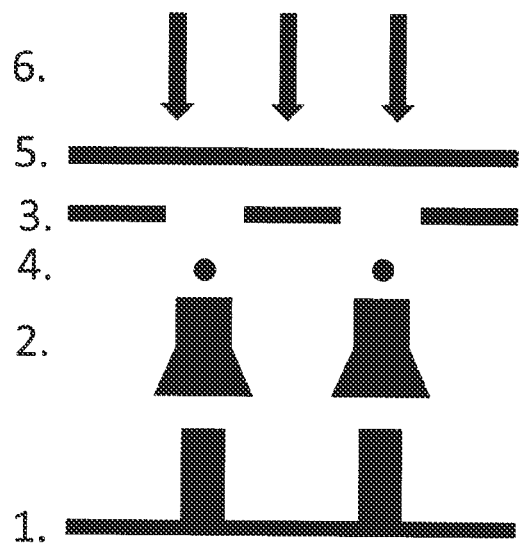
FIG. 2b shows a second embodiment of the procedure according to the solution.
Figure 2C:
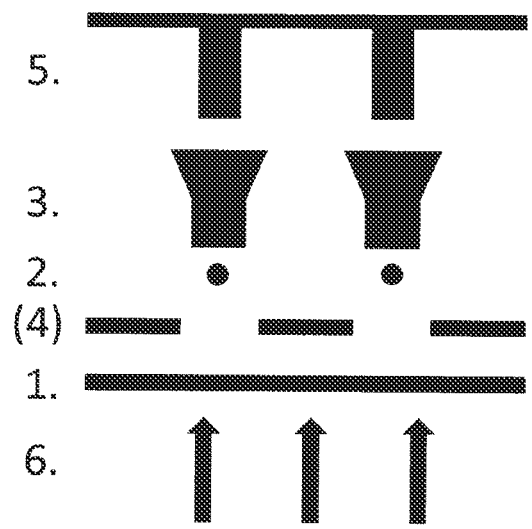
FIG. 2c a third embodiment of the method according to the solution.

FIGS. 2b and 2c illustrate the embodiment of this method, which allows batch membrane production.

In the embodiment of the method shown in FIG. 2b, the following steps are performed: 1) providing a single stamp or an array of multiple stamps, the stamp or stamps being vertically oriented; 2) assigning at least one insert blank to each stamp, the stamp being positioned centrally in the respective insert blank; in assigning the insert blank and stamp, the insert blank may be z. When assigning the insert blank and stamp, the insert blank can be put over the stamp or the stamp is inserted into the insert blank; 3) Arrangement of a fastening mechanism (clamping mechanism, e.g.e.g. with springs) to connect the insert blank with the respective stamp; 4) introducing a quantity of printing fluid (with the starting materials for membrane production) into the insert blank via the free opening (e.g. with a pipette); 5) covering the free openings of the insert blanks, preferably with a foil (PDMS foil), 6) forming a polymer membrane by irradiation (irradiation preferably from above through the foil); 7) removing the PDMS foil; 8) Remove the mounting mechanism, and 9) Remove the stamp or stamp array.

In the method embodiment shown in FIG. 2c, the sequence of method steps in the batch method is changed: 1) providing a film (e.g. PDMS film); 2) providing an aliquot of starting materials for membrane production at the position on the film which is intended for one feed blank at a time (using a pipette or multipipette); 3). arranging an insert blank around the respective aliquot of membrane forming starting materials on the film; 4) arranging a fastening mechanism to fasten the insert blank to the film; 5) inserting a single die or an array of multiple dies into the respective insert blank, the die or dies being vertically oriented; 6) forming a polymer membrane by irradiation (preferably from below through the film); 7) removing the stamp or stamp array from the insert blank; and 8) removing the insert blank with the polymer membrane formed therein. The insert blanks provided with the polymer membrane can then be stored e.g. in multiwell plates.

Figure 3:
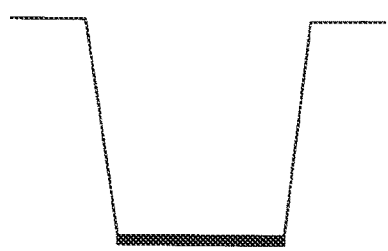
FIG. 3 shows a fourth embodiment of the method according to the solution.
Figure 3:
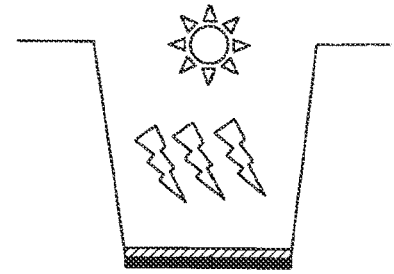
Figure 3:
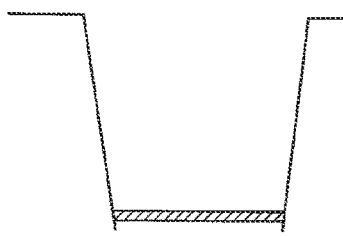
Figure 3:
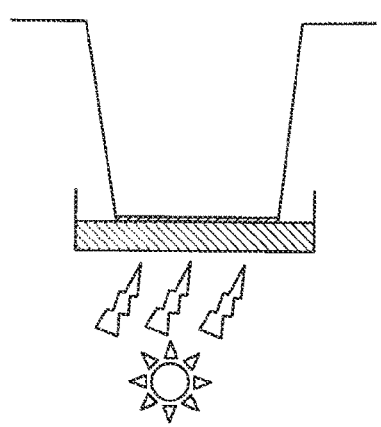
Figure 3:
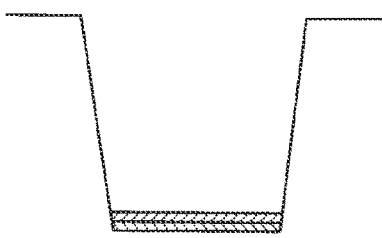
Figure 3:
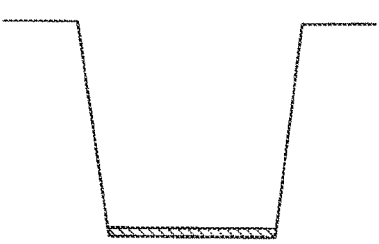
Figure 3:
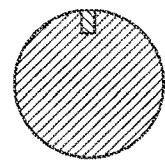
Figure 3:
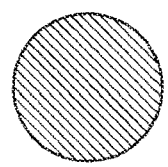

The fourth embodiment of the method shown in FIG. 3 uses a disc instead of a stamp as spacer. In a first step, the disc is inserted into the culture insert and defines the thickness of the membrane to be formed by the distance to the lower opening of the culture insert. In a second step, after the desired membrane height has been determined by the disc as a spacer, a polymerizable liquid is introduced into the culture insert. This liquid is then cured by light irradiation or a similar physicochemical method to form an auxiliary membrane.

After the auxiliary membrane has cured, the disc is removed again as a spacer in a third step, leaving behind a stable auxiliary membrane with an opening as a "bubble trap".

In the next, fourth step, the culture insert with the auxiliary membrane is placed in a reaction vessel containing the liquid biopolymer and then cured by irradiation in a printing method.

After hardening of the biomembrane and removal of the culture insert from the reaction vessel, a bilayer of biomembrane and auxiliary membrane remains in the culture insert. In a final step, the auxiliary membrane is removed by a physicochemical method or simple dissolution, leaving behind a flat biomembrane.

Figure 4A:
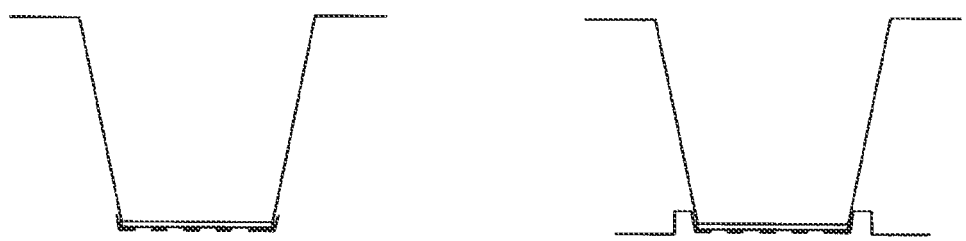
FIG. 4A shows a schematic illustration of how the manufactured membrane is secured in the culture insert.
Figure 4A:
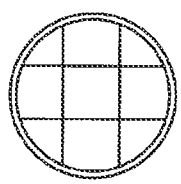
Figure 4A:
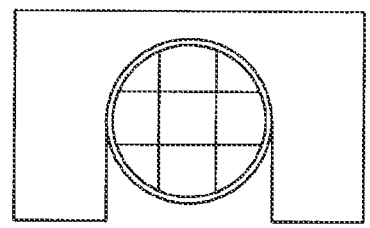
Figure 4B:
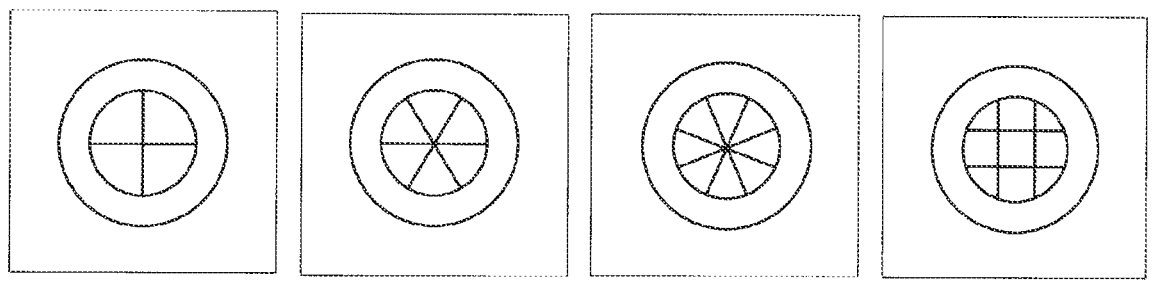
FIG. 4B shows a schematic representation of the different types of the securing device in FIG. 4A.

To prevent the printed membrane layer from falling out, a plastic grid can be placed under the culture insert after the biomembrane has been manufactured (see FIG. 4A). The biomembrane is held or secured by a grid that is secured with an interference fit at the base of the culture insert. The biomembrane retainer can be easily removed with a cap lifter to allow access to or removal of the biomembrane. The securing device can be either a grid or a spoke-shaped device (see FIG. 4B).

Figure 5:
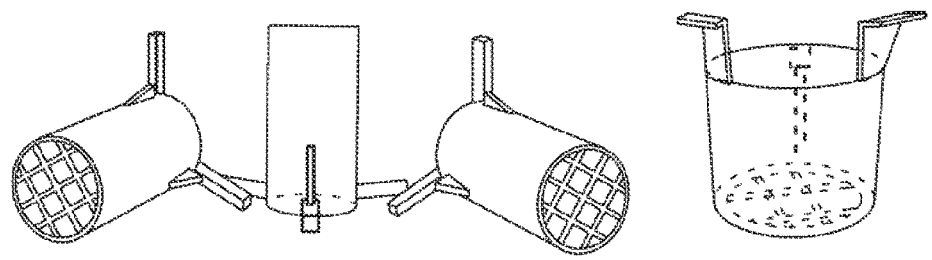
FIG. 5 shows a first embodiment of the cell culture insert manufactured according to the solution.

An embodiment of a cell culture insert manufactured according to the solution is shown in FIG. 5. Here the cell culture insert is cylindrical in shape. The upper opening is provided with support bars, which allow the cell culture insert to be inserted into and removed from a nutrient solution in a multiwell plate. At the lower opening, a grid is visible as a safety device to hold the biomembrane in the cylindrical housing.

Figure 6A:
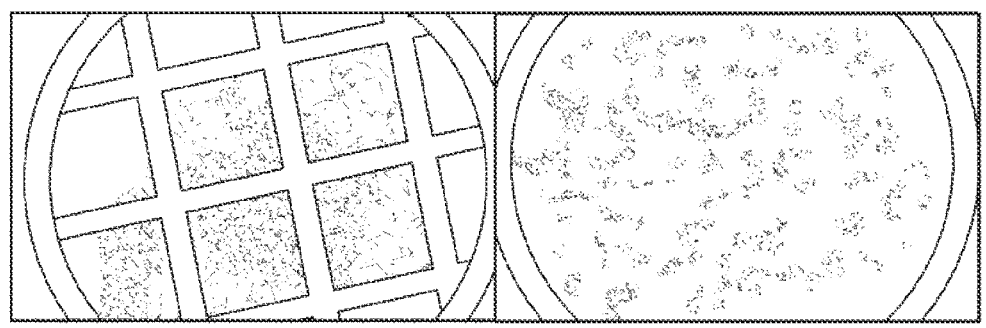
FIG. 6A shows membrane of a cell culture insert cultivated with cells according to the solution.
Figure 6B:
FIG. 6B shows a cross-sectional image of a membrane populated with cells in a cell culture insert according to the solution.

Depending on the membrane material, different cells can colonize the biomembrane and form monolayers (see FIGS. 6A and 6B).

The illustrations of FIG. 6A show microscopic transmitted light images of the top and bottom side of a colonized carrier. On the left, the bottom side is shown with a holder for the membrane, on the right the top side of the carrier with colonized surface. The cells used were Caco-2 cells.

FIG. 6B shows a lateral cross-section of a gelatine membrane populated with HUVEC cells, performed with a 2-photon microscope. The individual colors show the different markers that were examined in this experiment: DAPI (cell nucleus), vWF and CD31 (vascular cell marker). A polarization and thus a natural behavior of the cells can be detected.

Figure 6C:
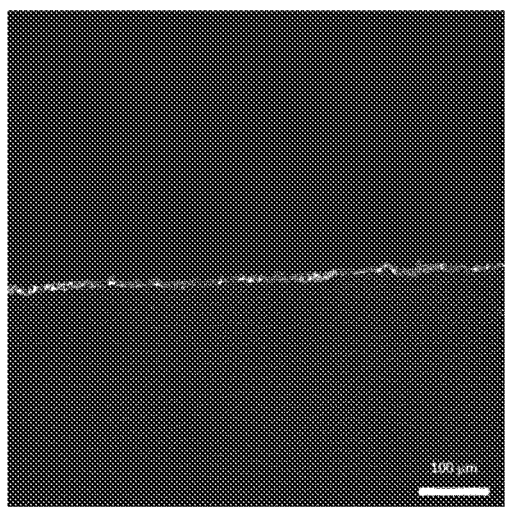
FIG. 6C shows microscopic images of a membrane populated with cells in a cell culture insert according to the solution.
Figure 6C:
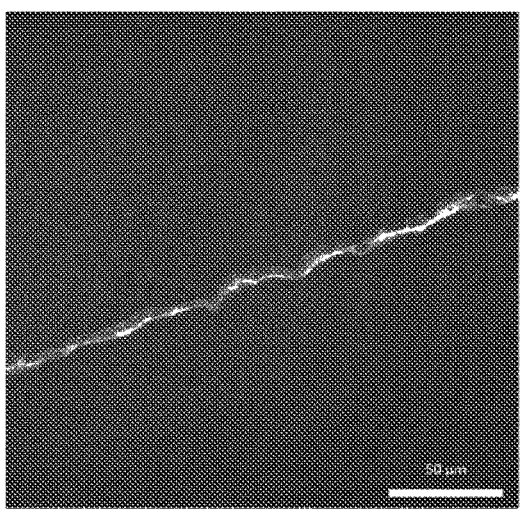
Figure 6C:
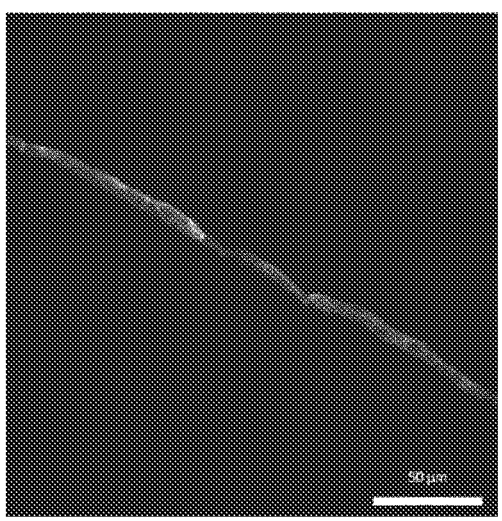

The microscopic images shown in FIG. 6C show a lateral section through the membrane. The upper side of the image represents the top side of the membrane, the cell-populated membrane divides the image, and the lower half of the image represents the bottom side of the carrier. The individual stains indicate a polarization of the cells towards the membrane. In the case of the microscopic image an increased collagen production of the cells towards the membrane can be shown. The cells are Vero cells. In addition, the cell nuclei were also stained with DAPI. The aim of the experiment was to show a polarization and interaction of the cells. In comparison, this effect is less pronounced in a Petri dish or not at all.

In the following two images, the markers ITGB1 (right) and aPKC (bottom left) were examined, which also document a polarization towards or away from the membrane.

Figure 7A:
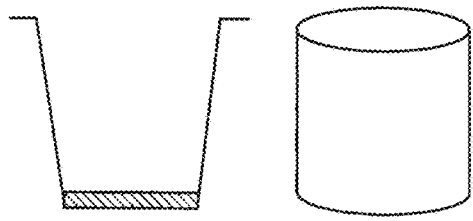
FIG. 7 shows a further embodiment of the cell culture insert manufactured according to the solution.
Figure 7B:
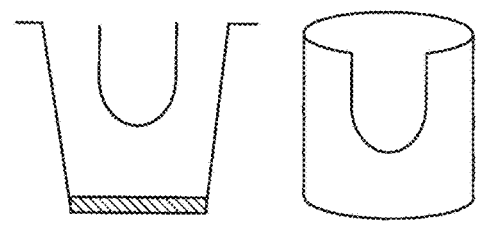
Figure 7:
Figure 7:
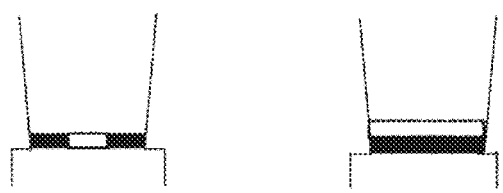
Figure 7:
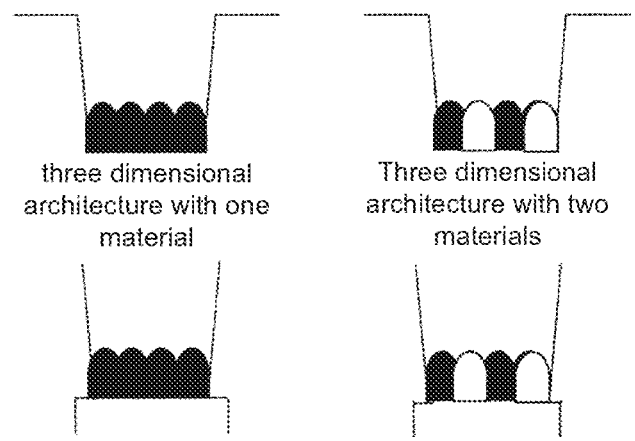
Figure 7:
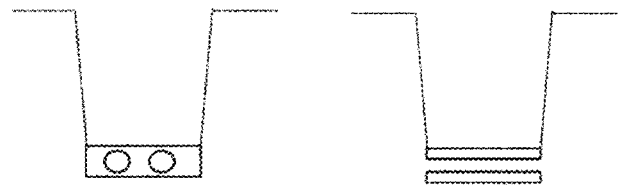
Figure 7:
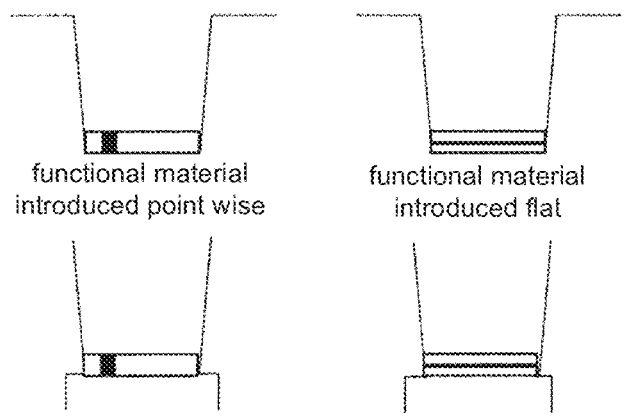
Figure 7K:
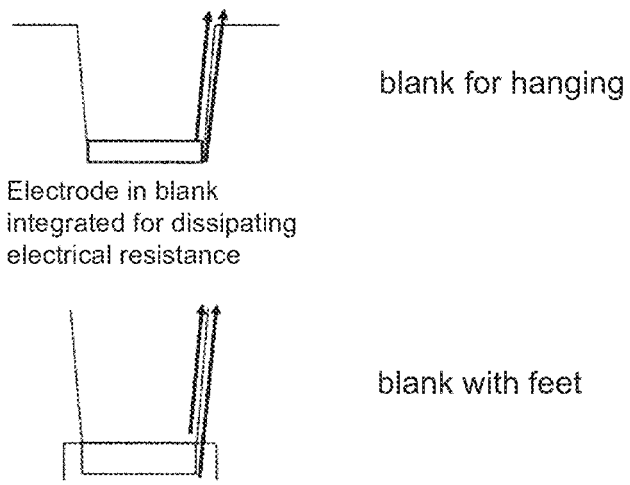

The present cell culture insert can be designed with a continuous rim (FIG. 7, a) for a barrier function or a cut-out (FIG. 7, b). The cutout can be located below the media level in the multiwell, so that the cells on the membrane can be supplied with nutrients.

The cell culture insert can be provided with two or more different materials as a membrane in a blank, whereby the materials can be arranged in different architectures, e.g. side by side (FIG. 7, c) or on top of each other (FIG. 7, d) or in other architectures. This architecture can be placed in blanks for hanging or with feet.

In another variant of the cell culture insert, the membrane is printed with a geometric shape. The membrane must not only be inserted straight into the blank, but can also have an architectural shape. For example, villi, channels, hills, valleys (FIG. 7, e) can be inserted, even if they are made of different materials (FIG. 7, f). This architecture can be inserted in blanks for hanging or with feet.

A channel may be introduced into the membrane of the cell culture insert, which can be flushed from outside the blank (FIG. 7, g, h). The channel can be used to supply the inner compartment of the blank. The channel acts as a medium carrier with culture medium, which is flushed through the channel. Cells that are located on the membrane inside the compartment can be supplied through the membrane.

Functional material may also be incorporated into the membrane of the cell culture insert. For example, an additional detector, dye, enzyme, chemokine, nanoparticles or similar can be integrated into the membrane during the printing method. Over time, this material can be used for online monitoring of the cell culture. For example, cell death can be detected by a fluorescent dye or the current oxygen saturation or pH value. The functional material may or may not have contact to the inner and outer boundary layer. The functionalization can be observed by a color change, irradiation or other detectable measurement. The functional material can be introduced pointwise into the membrane (FIG. 7, i) or flat (FIG. 7, j).

The cell culture insert can also enable the measurement of membrane density by electrical resistance. In this case, a special blank can be used in which a probe is attached to the inside and outside of the blank in order to measure the electrical resistance and thus draw conclusions about the density of the membrane and the cell layer (FIG. 7, k).

Figure 8:
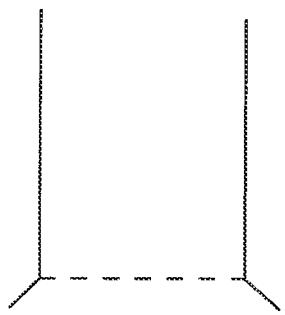
FIG. 8 shows a further embodiment of the cell culture insert manufactured according to the solution.

FIG. 8 shows a cell culture insert with outwardly directed and angled projections (feet) on its lower side or end (i.e. the part of the cell culture insert that contacts the bottom of the multiwell plate). This allows the cell culture insert to stand upright in the multiwell plate automatically.

Figure 9:
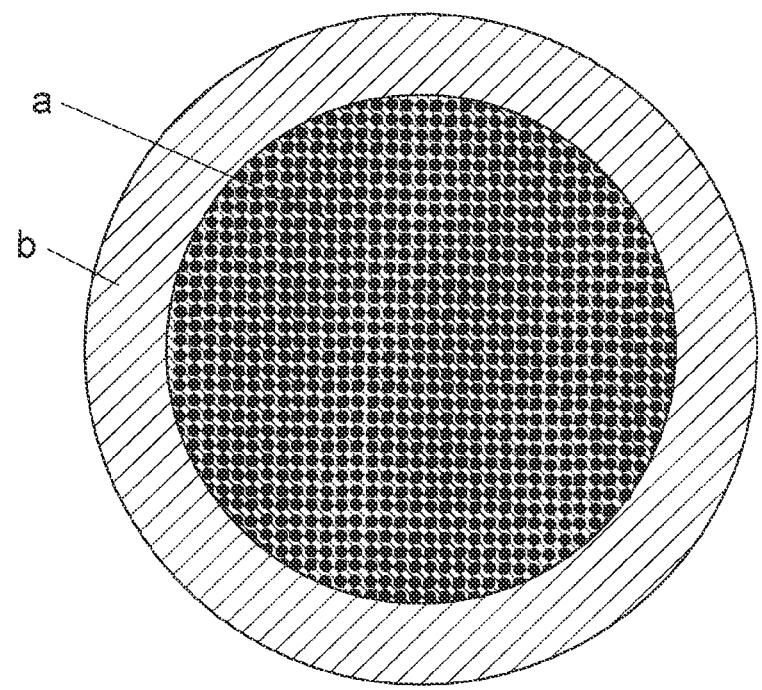
FIG. 9 shows an even further embodiment of the cell culture insert manufactured according to the solution.
Figure 9:
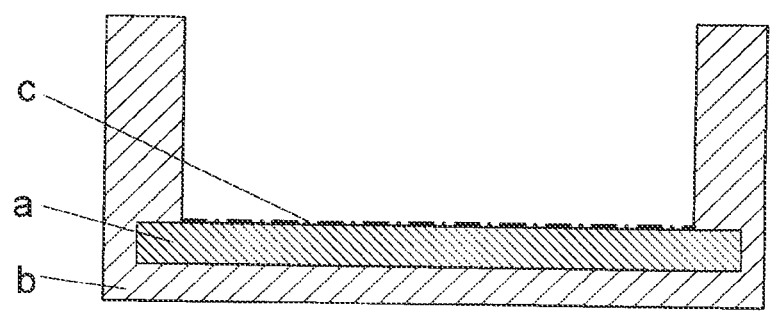

FIG. 9 shows another variation of the cell culture insert. In this variant of the cell culture insert two biomaterials are used, which can differ in their properties. The cell culture insert consists of a cylinder with a bottom (see figure Biopolymer 2, blue). On the bottom another biopolymer is incorporated (see figure Biopolymer 1, green). Material b (see figure) forms the framework that gives the construct stability. In the example, the biopolymer is based on polyethylene glycol (PEG), a biocompatible but cell-repellent polymer. Material b incorporates material a, which in the example is based on gelatine. In contrast to PEG, gelatine is not only biocompatible but also biofunctional, so that cells grow on this material. The combination of both materials creates a scaffold that can be colonized with cells in a directed manner. The area comprising biopolymer 1 (a) determines the maximum area on which cells can grow. During colonization, the cells grow to the edge. Since the border consists of the cell-repellent polymer 2 (b), they cannot colonize the border. The growth stops at this border.

EXAMPLE

Cell culture inserts with a diameter of 12 mm were produced using the stamping method. A gelatine matrix with a concentration of 10% (W/V) was used, mixed with LAP as initiator in a concentration of 0.1% (W/V). Furthermore, collagen I was used as an additive.

The blank was filled with a silicone stamp and placed in a basin in the printer containing the liquid gelatine matrix described above, so that the blank rests on the bottom of the basin in the printer. To create a membrane of 500 µm, the distance was adjusted accordingly with the stamp before.

Subsequently, the gelatine matrix was cured by irradiation with a wavelength of 385 nm. After hardening, the carrier was removed from the basin and the printer. In addition, the stamp was removed, leaving behind a cell culture insert with the previously defined height and with a flat surface for colonization.

Two different cell culture inserts were produced. A first insert with a membrane with collagen I as an additive and a second insert with a membrane without this additive. In this case the gelatine membrane was made transparent and could be examined optically.

After production of the cell culture inserts with biological membrane, they were colonized with Vero cells. This is a kidney cell line of the green monkey. This cell line is often used for infection experiments. After colonization, the Vero cells formed a confluent monolayer over the entire surface of the cell culture insert.

After colonization, a GFP-tagged cowpox strain was used to infect the Vero cells with the strain. The spread of the infection could be studied and observed by the fluorescent viruses and the transparent cell culture insert over the course of the experiment of 28 days.

After the experiment, the membrane was stamped out and deep-frozen. In addition, the membrane could be cut and stained with the usual histological methods, so that a histological follow-up was possible.

The invention claimed is:
1. A method for the preparation of a cell culture insert having at least one biological membrane, the method comprising the following steps:
 providing at least one hollow insert blank with a lower and an upper opening;
 inserting and arranging at least one spacer into the at least one hollow insert blank at a predetermined distance from the lower opening of the at least one hollow insert blank, wherein the predetermined distance is determined by a thickness of the at least one biological membrane to be produced in the at least one hollow insert blank;
 introducing starting materials for production of the at least one biological membrane into the at least one hollow insert blank provided with the at least one spacer;

forming the at least one biological membrane in the at least one hollow insert blank using a bio-printing method; and removing the at least one spacer from the at least one hollow insert blank, leaving the formed at least one biological membrane in the at least one hollow insert blank.

2. The method according to claim 1, wherein the at least one spacer is provided with at least one opening which allows gas bubbles to escape from the at least one biological membrane.

3. The method according to claim 1, wherein the at least one spacer is in the form of a stamp.

4. The method according to claim 1, wherein the at least one circular spacer is formed as a disc.

5. The method according to claim 1, wherein the at least one spacer is used in combination with an auxiliary membrane.

6. The method according to claim 5, wherein the auxiliary membrane is formed on an upper side of the at least one circular spacer by introducing a liquid composition containing starting materials suitable for forming the auxiliary membrane and subsequent curing.

7. The method according to claim 5, wherein the at least one spacer is removed after the auxiliary membrane has cured.

8. The method according to claim 5, wherein the at least one hollow insert blank provided with the auxiliary membrane is placed in a container containing the starting materials for producing the at least one biological membrane, the at least one biological membrane is formed, and the auxiliary membrane is removed from the at least one hollow insert blank by suitable physicochemical methods, the formed at least one biological membrane remaining in the at least one hollow insert blank.

9. The method according to claim 1, wherein the at least one biological membrane comprises: technical biopolymers; alpha- and beta-polysaccharides; lipids; polyhydroxyalkanoates; bio-based polymers; petroleum-based polymers; and components of extracellular matrix.

10. The method according to claim 1, wherein a securing means is provided for holding the at least one biological membrane in place in the at least one hollow insert blank.

11. The method according to claim 10, wherein the securing means is in the form of a carrier consisting of different structures and adapted to the at least one biological membrane material.

12. A method for the preparation of a cell culture insert having at least one biological membrane, the method comprising the following steps:

providing at least one hollow insert blank with at least one opening;

covering the at least one opening of the at least one hollow insert blank with a cover and introducing starting materials for producing the at least one biological membrane into the at least one hollow insert blank through a different opening of the at least one hollow insert blank forming at least one biological membrane in the at least one hollow insert blank using a bio-printing method; and removing the cover from the at least one opening, leaving the formed at least one membrane in the at least one hollow insert blank.

13. The method according to claim 12, wherein the at least one biological membrane comprises: technical biopolymers; alpha- and beta-polysaccharides; lipids; polyhydroxyalkanoates; bio-based polymers; petroleum-based polymers; and components of extracellular matrix.

14. The method according to claim 12, wherein a securing means is provided for holding the at least one biological membrane in place in the at least one hollow insert blank.

15. The method according to claim 14, wherein the securing means is in the form of a carrier consisting of different structures and adapted to the at least one biological membrane material.

16. A method for the preparation of a cell culture insert having at least one biological membrane, the method comprising the following steps:

providing at least one hollow insert blank with at least one opening; and placing the at least one hollow insert blank in a container containing starting materials for producing the at least one membrane;

forming at least one biological membrane in the at least one hollow insert blank using a bio-printing method; and removing the at least one hollow insert blank from the container, leaving the formed at least one biological membrane in the at least one hollow insert blank.

17. The method according to claim 16, wherein the at least one biological membrane comprises: technical biopolymers; alpha- and beta-polysaccharides; lipids; polyhydroxyalkanoates; bio-based polymers; petroleum-based polymers; and components of extracellular matrix.

18. The method according to claim 16, wherein a securing means is provided for holding the at least one biological membrane in place in the at least one hollow insert blank.

19. The method according to claim 18, wherein the securing means is in the form of a carrier consisting of different structures and adapted to the at least one biological membrane material.

* * * * *

UNITED STATES PATENT AND TRADEMARK OFFICE
CERTIFICATE OF CORRECTION

| | | |
|---|---|---|
| PATENT NO. | : 12,162,212 B2 | Page 1 of 1 |
| APPLICATION NO. | : 17/054810 | |
| DATED | : December 10, 2024 | |
| INVENTOR(S) | : Lutz Kloke et al. | |

It is certified that error appears in the above-identified patent and that said Letters Patent is hereby corrected as shown below:

In the Claims

Column 15, Line 15, Claim 4, after "one" delete "circular"

Signed and Sealed this
Eleventh Day of February, 2025

Coke Morgan Stewart
*Acting Director of the United States Patent and Trademark Office*